United States Patent [19]

Ogawa et al.

[11] Patent Number: 5,684,026

[45] Date of Patent: Nov. 4, 1997

[54] AMINOCYCLOPENTANE DERIVATIVE

[75] Inventors: Seiichiro Ogawa, Tokyo; Chikara Uchida, Aichi; Hiroshi Kimura, Saitama; Jin-ichi Inokuchi, Tokyo, all of Japan

[73] Assignee: Seikagaku Kogyo Kabushiki Kaisha (Seikagaku Corporation), Tokyo, Japan

[21] Appl. No.: 561,947

[22] Filed: Nov. 22, 1995

[30] Foreign Application Priority Data

Nov. 22, 1994 [JP] Japan .................................. 6-311264

[51] Int. Cl.$^6$ .......................... A01N 43/76; A61K 31/42; C07D 261/20; C07D 263/62
[52] U.S. Cl. ........................ 514/377; 548/217; 548/233; 548/234
[58] Field of Search .................................. 548/217, 233, 548/234; 514/377

[56] References Cited

U.S. PATENT DOCUMENTS 5,260,447  11/1993  Nakajima et al. .................... 548/222

OTHER PUBLICATIONS

Ogawa et al, *Chemistry Letters*, pp. 173–176, The Chemical Society of Japan (1993).
Uchida et al, *J. Chem. Soc. Perkin Trans.*, 1:589–602 (1994).
"Synthesis and Trehalase-Inhibitory Activity of 5'A-Carbatrehazolin" Carbohydrate Letters, vol. 1 pp. 77–81 (1994).
Bioorganic & Medical Chemistry Letters, vol. 4 No. 22 pp. 2643–2648 1994 "Potent Glycosidase Inhibitors, N–Phenyl Cyclic Isourea Derivitives of 5–Amino–and 5–Amino–1–C (hydroxmethyl)–cyclopentene–1,2,3,4–tetralos" (1994).
"Synthesis of trehazolin analogues containing modified sugar moities", Department of Applied Chemistry, Faculty of Science and Technology, Keio University, Hiyoshi, Kohoku–ku, Yokohama 223 Japan (1995).
"Synthesis of Trehazolin Analogues containing Modified Aminocyclitol Moieties", Department of Applied Chemistry, Faculty of Science and Technology, Keito University, Hiyoshi Kohoku–ku, Yokohama, 223 Japan (1994).
"Synthesis of Aminocyclitol Moieties of Trehalase Inhibitors, Trehalostatin and Trehazolin. Correct Structure of the Inhibitor" Department of Applied Chemistry, Faculity of Science and Technology, Keio University, Hiyoshi, Yokohama 223, Japan (1992).

(List continued on next page.)

*Primary Examiner*—Johann Richter
*Assistant Examiner*—Jane C. Oswecki
*Attorney, Agent, or Firm*—Sughrue, Mion, Zinn, Macpeak & Seas, PLLC

[57] ABSTRACT

The present invention provides aminocyclopentane derivatives which are saccharide analogs having extremely high α-glucosidase inhibitory effects and novel structures and expected to be usable or applicable to drugs or agricultural chemicals. An aminocyclopentane derivative represented by the formula (1), wherein $R_1$ represents H while $R_2$ represents $CH_2OH$, or $R_1$ represents $CH_2OH$ while $R_2$ represents H and $R_3$ represents a substituted or unsubstituted aryl group or an alkyl, alkenyl, alkynyl or hydroxyalkyl group having 1 to 10 carbon atoms, intermediates for the synthesis of the same, a process for producing the intermediates and a process for producing the aminocyclopentane derivative.

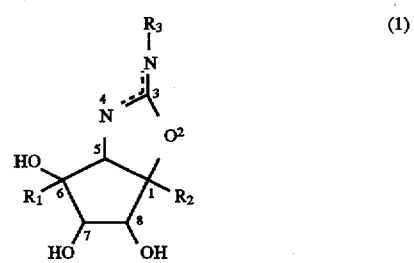

11 Claims, 2 Drawing Sheets

OTHER PUBLICATIONS

"Total Synthesis of the Trehalse Inhibitors Trehalostien and Trehazolin, and of Their Diastereoisomers. Final Structural Confirmation of the Inhibitor" Department of Applied Chemistry, Faculty of Science and Technology, Keio University, Hiyoshi, Kohoku–ku, Yokohama, 223 Japan (1994).

"Synthesis of Aminocyclitol Moieties of Trehalase Inhibitors, Trehalostain and Trehazolin. Confirmation of the Correct Structure of the Inhibitor" Department of Applied Chemistry, Faculty of Science and Technology, Keio University, Hiyoshi, Yokohama 223, Japan (1992).

"A (1→4)–Trehazoloid Glucosidase Inhibitor with Aglycon Selectivity," Spencer Knapp, Ashok Purandare, Karen Rupitz and Stephen G. Withers, *J. Am. Chem. Soc.* 1994, 116, 7461–7462.

AMINOCYCLOPENTANE DERIVATIVE

FIELD OF THE INVENTION

This invention relates to aminocyclopentane derivatives of novel structures and intermediates for the synthesis of the same. More particularly, it relates to glycosidase inhibitors.

BACKGROUND OF THE INVENTION

Recent studies have clarified the biological functions of sugar chains located in the surface layer of cells. As a result, inhibitors of enzymes, which construct or decompose these sugar chains, have attracted public attention and thus studies on the synthesis thereof have been widely made by chemists. In recent years, moreover, it has become the focus of attention to develop inhibitors which are specific for various glycosidases. For example, attempts have been made to develop a compound which inhibits not maltase but sucrase, though these enzymes are both α-glucoside hydrolase, or a compound which inhibits not an enzyme originating animals but another one originating in insects. An approach to these objects, which is commonly employed at the present stage, comprises modeling the structure of an inhibitor after the sugar chain which is actually hydrolyzed by the target enzyme in vivo. Thus there have been applied so-called saccharide analogs to glycoside hydrolase inhibitors with simple structures employed as lead compounds. These saccharide analogs are classified into carbasaccharides, azasaccharides, thiasaccharides, phosphasaccharides, etc.

There are observed some compounds wherein the oligosaccharide chain thus designed and synthesized seemingly exhibits an inhibitory activity not on the aimed enzyme but on another enzyme. Regarding the development of specific inhibitors, therefore, the lead compounds known hitherto suffer from various problems. In order to solve these problems, a number of novel lead compounds have been synthesized and screened. C-H. Wong et al. are now extending the scope of their studies from azapyranose [G. C. Lock, C. H. Fotsh and C-H. Wong, Acc. Chem. Res., 26, 182–190 (1993)] to azafuranose [Y-F. Wang, Y. Takaoka and C-H. Wong, Angew. Chem. Int. Ed. Engl., 33, 1242–1244 (1994)]. Recently, it has been reported that an amidine skeleton inhibits glycosidases. Thus attempts have been made to introduce an azasaccharide into an oligosaccharide chain via this amidine skeleton [a) G. Papandreou, M. K. Tong and B. Ganem, J. Amer. Chem. Soc., 115, 11682–11690 (1993); b) Y. Bleriot, A. Genre-Grandpierre and C. Tellier, Tetrahedron Lett., 35, 1867–1870 (1994)].

On the other hand, α-glucoside hydrolases include α-glucosidases I and II which act on the process of the biosynthesis of glycoproteins contained in cells in addition to amylase, maltase, isomaltase, sucrase and trehalase. Recently, it has been energetically attempted to apply inhibitors of these enzymes to drugs and agricultural chemicals and some inhibitors are now commercially available in practice. For example, acarbose, which is an inhibitor of α-amylase and sucrase, is marketed as an antidiabetic agent or an antiobestic agent (tradename: Glucobay, manufactured by Bayer), while validamycins, which inhibit trehalase, are marketed as an agricultural chemical agianst stripe (tradename: Validacin, Takeda Chemical Industries, Ltd.) and expected to be efficacious as an insecticide. In United States, furthermore, deoxynojirimycin derivatives are subjected to clinical tests as drugs (antiviral agents). Furthermore, studies are now under way to utilize inhibitors as tools for the clarification of the unknown functions of enzymes. Recently, it has been further reported that deoxynojirimycin (DNJ) is effective on AIDS. Namely, glucosidase inhibitors have become the focus of attention and, at the same time, it has been urgently required to develop enzyme inhibitors of novel structures applicable to drugs and agricultural chemicals.

SUMMARY OF THE INVENTION

An object of the present invention is to provide aminocyclopentane derivatives which are saccharide analogs with novel structures having extremely high α-glucosidase inhibitory effects and expected to be usable or applicable to drugs or agricultural chemicals.

The present invention provides:

(1) An aminocyclopentane derivative represented by the formula (1):

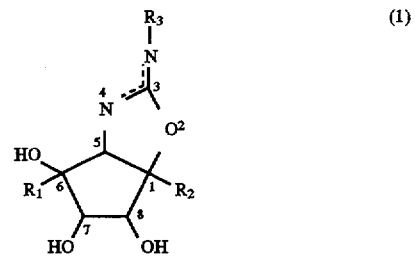

wherein $R_1$ represents H while $R_2$ represents $CH_2OH$, or $R_1$ represents $CH_2OH$ while $R_2$ represents H; and $R_3$ represents a substituted or unsubstituted aryl group or an alkyl, alkenyl, alkynyl or hydroxyalkyl group having 1 to 10 carbon atoms.

(2) An aminocyclopentane derivative as described in the above (1) wherein, in the aminocyclopentane derivative represented by the formula (1), $R_3$ represents a substituted or unsubstituted aryl group.

(3) An aminocyclopentane derivative as described in the above (2), wherein the aminocyclopentane derivative represented by the formula (1) is selected from the group consisting of (1S,5R,6S,7S,8R)-6-hydroxymethyl-3-phenylamino-2-oxa-4-azabicyclo[3.3.0]oct-3-ene-6,7,8-triol represented by the following structural formula (1-1L), (1R,5S,6R,7R,8S)-6-hydroxymethyl-3-phenylamino-2-oxa-4-azabicyclo[3.3.0]oct-3-ene-6,7,8-triol represented by the following structural formula (1-1D), (1S,5R,6S,7R,8S)-1-hydroxymethyl-3-phenylamino-2-oxa-4-azabicyclo[3.3.0]oct-3-ene-6,7,8-triol represented by the following structural formula (1-2L) and (1R,5S,6R,7S,8R)-1-hydroxymethyl-3-phenylamino-2-oxa-4-azabicyclo[3.3.0]oct-3-ene- 6,7,8-triol represented by the following structural formula (1-2D):

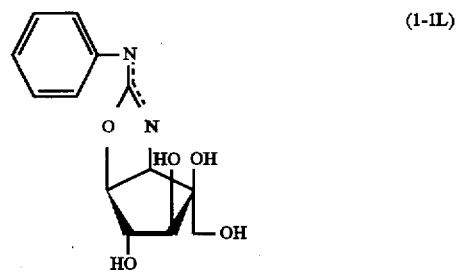

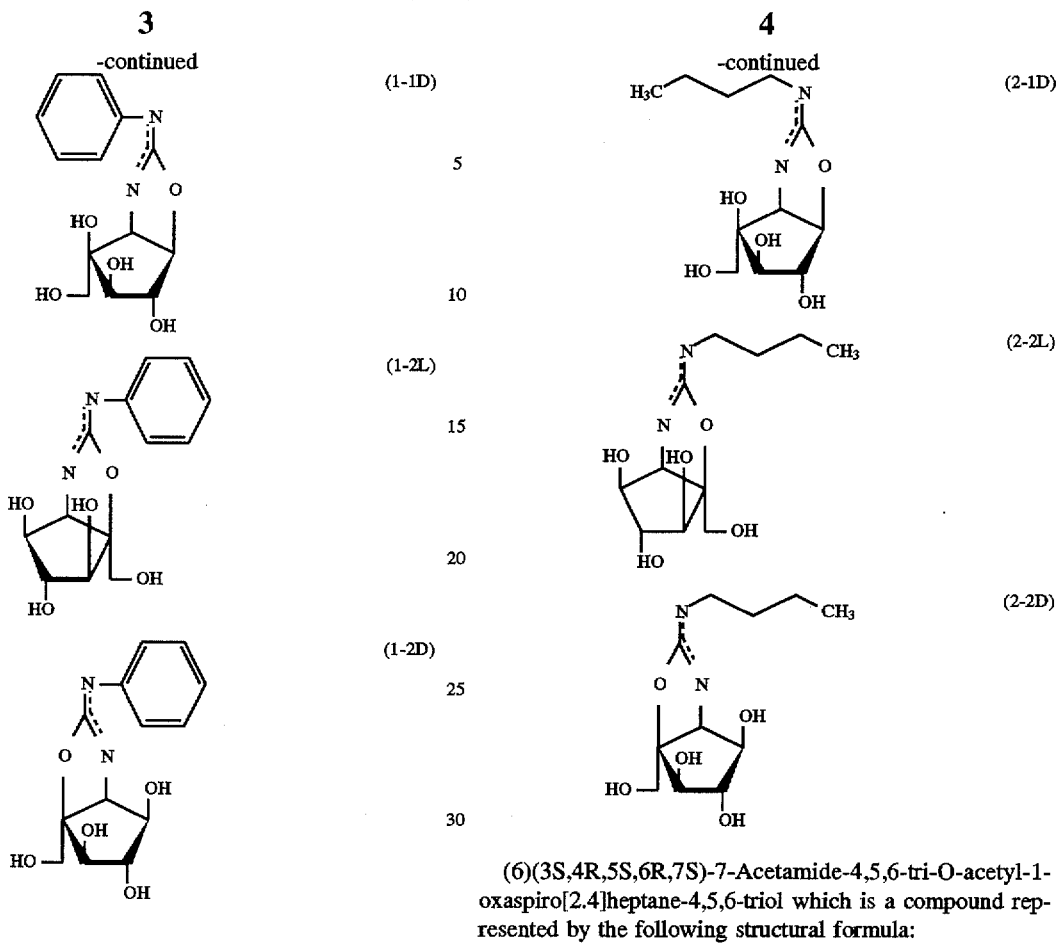

(4) An aminocyclopentane derivative as described in the above (1), wherein, in the aminocyclopentane derivative represented by an alkyl group having 1 to 10 carbon atoms.

(5) An aminocyclopentane derivative as described in the above (4), wherein the aminocyclopentane derivative represented by the formula (1) is selected from the group consisting of (1S,5R,6S,7S,8R)-6-hydroxymethyl-3-butylamino-2-oxa-4-azabicyclo[3.3.0]oct-3-ene-6,7,8-triol represented by the following structural formula (2-1L), (1R,5S,6R,7R,8S)-6 -hydroxymethyl-3-butylamino-2-oxa-4-azabicyclo[3.3.0]oct-3-ene-6,7,8-triol represented by the following structural formula (2-1D), (1S,5R,6S,7R,8S)-1-hydroxymethyl-3-butylamino-2-oxa-4-azabicyclo[3.3.0] oct-3-ene-6,7,8-triol represented by the following structural formula (2-2L) and (1R,5S,6R,7S,8R)-1-hydroxymethyl-3-butylamino-2-oxa-4-azabicyclo[3.3.0]oct-3-ene-6,7,8-triol represented by the following structural formula (2-2D):

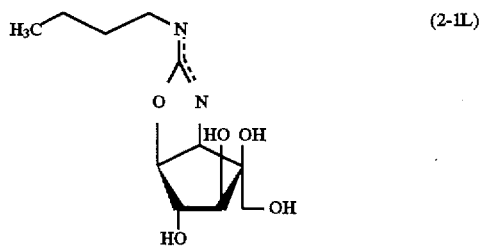

(6)(3S,4R,5S,6R,7S)-7-Acetamide-4,5,6-tri-O-acetyl-1-oxaspiro[2.4]heptane-4,5,6-triol which is a compound represented by the following structural formula:

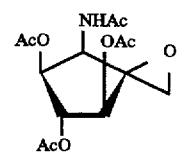

(7) An aminocyclopentane derivative represented by the formula (2):

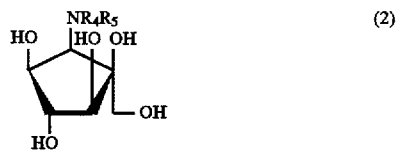

wherein $R_4$ and $R_5$ independently represent each H or a substituted or unsubstituted aryl group or an alkyl, alkenyl, alkynyl or hydroxyalkyl group having 1 to 10 carbon atoms.

(8) An aminocyclopentane derivative as described in the above (7), wherein the aminocyclopentane derivative represented by the formula (2) is selected from the group consisting of 1L-(1,2,4,5/3)-5-amino-1C-hydroxymethyl-1,2,3,4-cyclopentanetetraol represented by the following structural formula (d), 1L-(1,2,4,5/3)-5-dibutylamino-1-hydroxymethyl-1,2,3,4-cyclopentanetetraol represented by the following structural formula (d-1) and 1L-(1,2,4,5/3)-5-butylamino-1-hydroxymethyl-1,2,3,4-cyclopentanetetraol represented by the following structural formula (d-2):

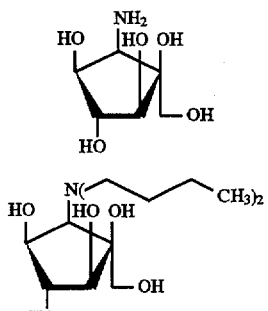

(9) 1D-(1,2,4,5/3)-5-Amino-1C-hydoxymethyl-1,2,3,4-cyclopentanetetraol which is a compound represented by the following structural formula:

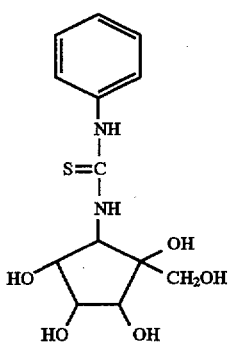

(10) N-[2-Hydroxymethyl-2,3,4,5-tetrahydroxycyclopentyl]-N'-phenylthiourea which is a compound represented by the following structural formula:

(11) A glycosidase inhibitor containing an aminocyclopentane derivative as described in the above (1) or (7) as an active ingredient.

(12) A glycosidase inhibitor as described in the above (11) wherein said glycosidase inhibitor is an α-glucosidase inhibitor.

(13) A glycosidase inhibitor as described in the above (12) wherein said active ingredient is an aminocyclopentane derivative as described in the above (2), (4) or (8).

(14) A glycosidase inhibitor as described in the above (13) wherein said active ingredient is an aminocyclopentane derivative as described in the above (3) or (5).

(15) A process for producing a compound as described in the above (6) which comprises oxidizing a compound represented by the following structural formula in a solution:

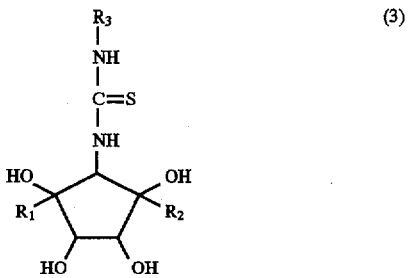

(16) A process for producing an aminocyclopentane derivative as described in the above (1) which comprises converting a thiourea compound represented by the formula (3) into cyclic isourea:

(3)

wherein $R_1$, $R_2$ and $R_3$ have the same definition as described in the above (1).

DETAILED DESCRIPTION OF THE INVENTION

Figure 1:
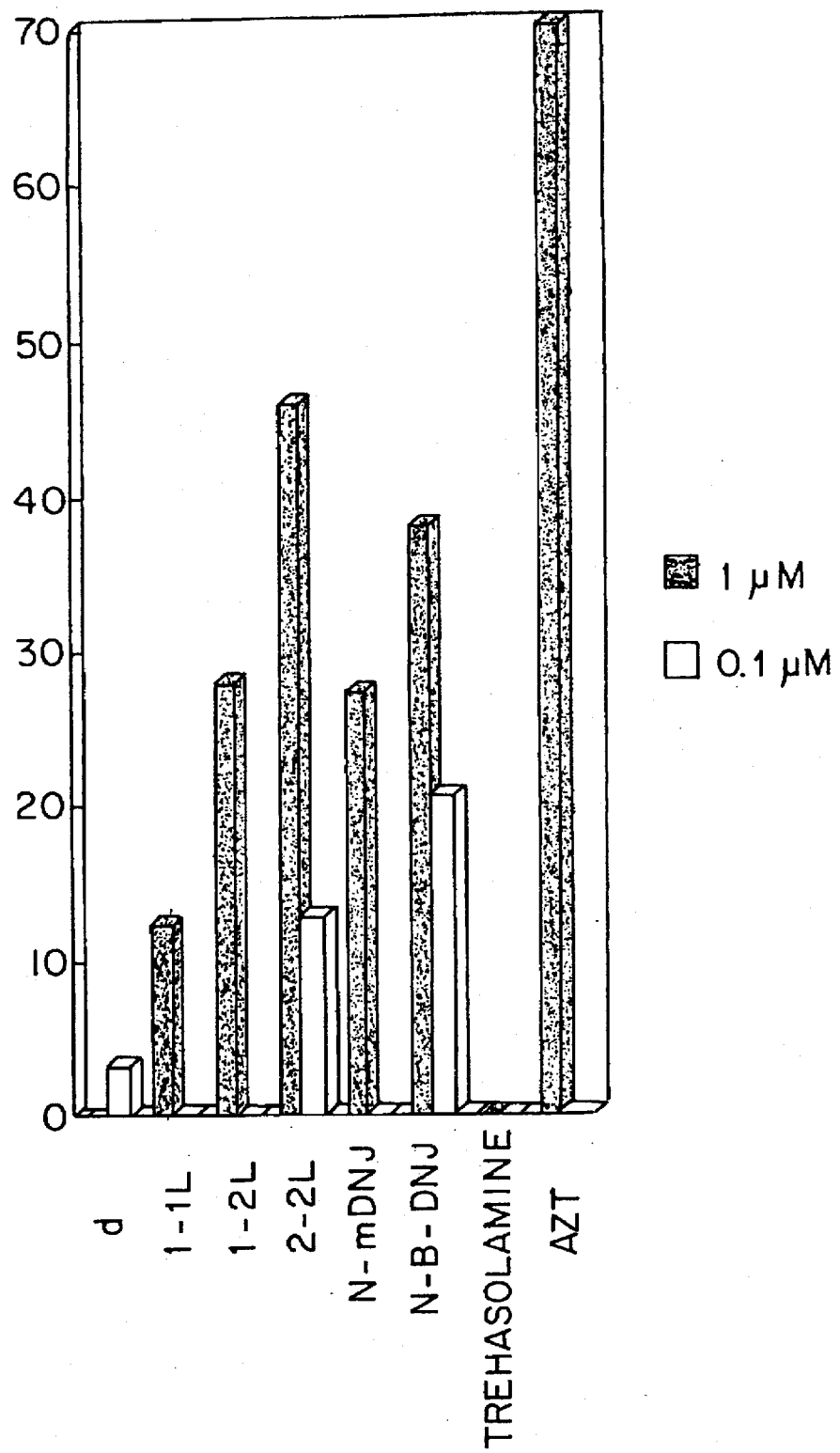
FIG. 1 is a graph showing the inhibitory effects on the production of HIV by PHA-activated PBMC infected with HIV.

The present invention will be described in detail below.

It is considered that the aminocyclopentane derivative of the present invention represented by the formula (1) [hereinafter referred to simply as the compound (1)] has tautomers as shown in the following formula. Thus, the broken line in the structural formula of the formula (1) stands for these tautomers. Also, the compound (1) involves arbitrary stereoisomers of the same.

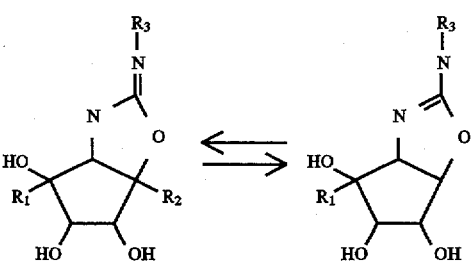

It is also considered that the orientation of the hydroxyl and hydroxymethyl groups in the compound (1), which has a bicyclo ring moiety containing a cyclic isourea bond, is a highly important factor and largely affects the enzyme inhibitory activity of the compound. It is assumed that the isourea moiety having two nitrogen atoms in the structure of this compound (1) is weakly basic and strongly binds to the active center when the compound (1) forms a complex with an enzyme. Thus the activity of specifically inhibiting the enzyme can be enhanced to an unprecedented level.

In the formula (1), $R_3$ represents a substituted or unsubstituted aryl group or an alkyl, alkenyl, alkynyl or hydroxyalkyl group having 1 to 10 carbon atoms, preferably 3 to 8 carbon atoms. It is preferable that $R_3$ is a phenyl group or a butyl group. Examples of the substituents of the aryl group include alkyl, alkenyl and alkynyl groups having 1 to 6 carbon atoms, halogen atoms and hydroxyl, nitro and carboxyl groups.

Preferable examples of the compound (1) of the present invention include the compounds (1-1), (1-2), (2-1) and (2-2) as shown below.

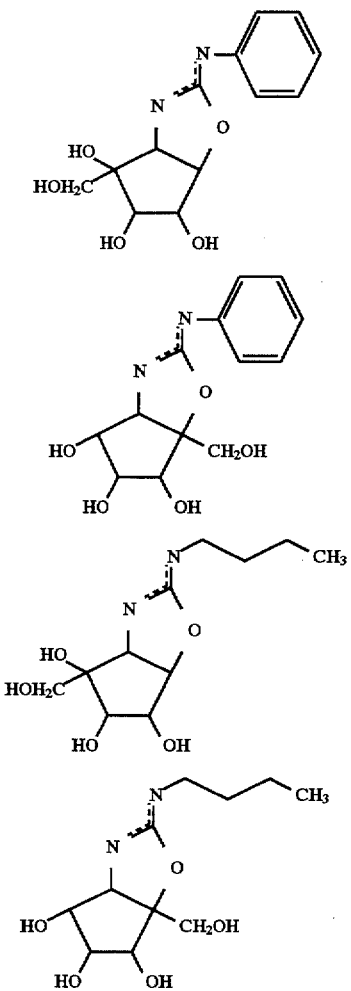

The compounds (1-1) and (1-2) are structurally isomeric with each other, while the compounds (2-1) and (2-2) are also structurally isomeric with each other. As described in the above (3), the compound (1-1) involves enantiomers represented by the structural formulae (1-1L) and (1-1D). Similarly, the compound (1-2) involves enantiomers represented by the structural formulae (1-2L) and (1-2D) as described in the above (3). Furthermore, the compounds (1-1) and (1-2) involves arbitrary diastereomers originating in the hydroxyl groups at the 6-, 7- and 8-positions. As described in the above (5), the compound (2-1) involves enantiomers represented by the structural formulae (2-1L) and (2-1D). Similarly, the compound (2-2) involves enantiomers represented by the structural formulae (2-2L) and (2-2D) as described in the above (5). Furthermore, the compounds (2-1) and (2-2) involve arbitrary diastereomers originating in the hydroxyl groups at the 6-, 7- and 8-positions.

The compounds (1-1) and (1-2) have activities of inhibiting glucosidases. In particular, they each exhibits an extremely high activity of inhibiting α-glucosidase. They also have anti-HIV activities. Similarly, the compounds (2-1) and (2-2) have activities of inhibiting glucosidases. In particular, they each exhibits an extremely high activity of inhibiting α-glucosidase. They also have anti-HIV activities.

The compounds (1-1L) and (1-2L) of the present invention can be synthesized in accordance with the following reaction scheme 1.

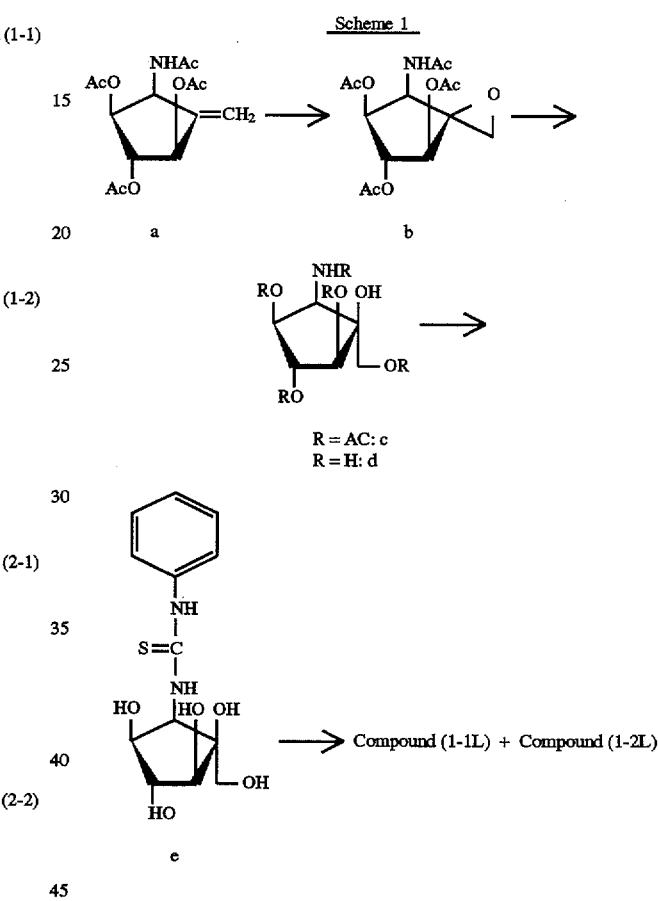

An olefine compound (i.e., the compound (a)) (synthesized by the method described in C. Uchida, T. Yamagishi and S. Ogawa, J. Chem. Soc., Perkin Trans. 1, 1994, 589–602) is dissolved in an organic solvent (preferably 1,2-dichloroethane) other than ketone. While maintaining the pH at the neutral level in the presence of an aqueous buffer solution, an oxidizing agent such as a peracid (for example, m-chloroperbenzoic acid, perbenzoic acid, monoperoxyphthalic acid, trifluoroperacetic acid, performic acid) or a peroxide (for example, dioxirane) is added thereto in 1 to 10 equivalent amount to the olefine compound at 0° C. to about the boiling point of the reaction mixture (under reflux). Alternatively, a metal catalyst capable of generating hydroperoxide [for example, vanadium pentaoxide ($V_2O_5$) /tert-butyl hydroperoxide (tBuOOH), sodium tungstate ($Na_2WO_4$)/hydrogen peroxide ($H_2O_2$), molybdenum pentaoxide($MoO_5$) hexamethyl-phosphorylamide (HMPA)/ tBuOOH] is added thereto at 0° C. to about the boiling point of the reaction mixture (under reflux). Then the resulting mixture is stirred for 0.5 to 120 hours in dark to thereby oxidize the starting compound (a). The reaction system is diluted with a non-alcoholic organic solvent (chloroform, ethyl acetate, etc.) and washed with an aqueous solvent (saturated aqueous solution of sodium thiosulfate, saturated aqueous solution of sodium hydrogencarbonate, etc.) to thereby give the compound (b) [(3S,4R,5S,6R,7S)-7-acetamide-4,5,6-tri-O-acetyl-1-oxaspiro[2.4]heptane-4,5,6-triol]. The obtained product may be further purified by chromatography, etc. Ac represents an acetyl group.

The compound (b) is dissolved in an aqueous solution of an organic solvent, such as aqueous solution of N,N-dimethylformamide (DMF), aqueous solution of dimethyl sulfoxide (DMSO) or aqueous solution of 2-methoxyethanol, followed by the addition of sodium acetate, sodium benzoate, etc. thereto. After stirring at room temperature to 150° C. for 1 to 48 hours, the reaction mixture was concentrated under reduced pressure. Then the resulting residue was acetylated with a base, such as pyridine, 4-dimethylaminopyridine, lutidine or triethylamine, and acetic anhydride, acetyl chloride, etc. After purifying by chromatography, etc., the compound (c) [1L-(1,2,4,5/3)-5-acetamido-1-acetoxymethyl-2,3,4-tri-O-acetyl-1,2,3,4-cyclopentanetetraol] is obtained as a syrup.

The compound (c) is deacetylated by dissolving in 0.5 to 6M hydrochloric acid or sulfuric acid and stirring at room temperature to 100° C. for 0.5 to 5 hours. After concentrating under reduced pressure, the resulting residue is purified with the use of a cation exchange resin [for example, Dowex 50W-X2, X4, X8 (trade name), Amberlite IR-120B, CG-50 (trade name)], etc. to thereby give the compound (d) [epitrehasolamine=1L-(1,2,4,5/3)-5-amino-1C-hydroxymethyl-1,2,3,4-cyclopentanetetraol] as a syrup.

In the route for the synthesis of the compound (d), alternatively, the compound (a) may be hydroxylated with osmium oxide (VIII) (OsO$_4$) in an aqueous solution of acetone, which is used in 1 to 5 equivalent amount to the compound (a), or 0.05 to 1 equivalent amount of OsO$_4$ and 1 to 5 equivalent amount of an oxidizing agent such as N-methylmorpholin-N-oxide for 1 to 72 hours, and then acetylated followed by the separation of the diastereomers of the compound (c) by silica gel chromatography to thereby give the compound (c) without forming the compound (b) as an intermediate (J. Chem. Soc. Perkin Trans. 1, 1994, 589–602).

The compound (d) is dissolved in an aqueous solution of an alcohol, etc. Then phenyl isothiocyanate is added thereto in 1 to 5 equivalent amount to the compound (d) and the resulting mixture is stirred at 0° to 80° C. for 1 to 72 hours. After concentrating the reaction mixture under reduced pressure, the resulting residue is usually purified by partition column chromatography to thereby give the phenylthiourea compound, i.e., the compound (e) [N-[(1R)-(1,2,3,5/4)-2-hydroxymethyl-2,3,4,5-tetrahydroxycyclopentyl]-N'-phenylthiourea] as a white solid.

The compound (e) is dissolved in a ketone or alcohol solvent. Then a catalyst [mercury oxide (yellow or red), lead oxide, alkyl iodide, triethyloxonium tetrafluoroborate, methyl triflate, a mixture of sodium hypochlorite with sodium hydroxide, a mixture of triphenylphosphine with diethyl azodicarboxylate, etc.] is added thereto in 1 to 10 equivalent amount to the compound (e) and the mixture is stirred at 0° C. to about the boiling point of the reaction mixture (under reflux) for 1 to 72 hours to thereby give a cyclic isourea compound. The reaction system is filtered through celite, etc. and washed with methanol, etc. The filtrate is combined with the washing liquor and concentrated under reduced pressure. The residue thus obtained is subjected to thin layer chromatography, etc., to thereby roughly separate isomers from each other. Thus crude 6-hydroxymethylisourea, i.e., crude compound (1-1L) is first obtained. This crude product is purified with the use of a cation exchange resin as described above to thereby give the compound (1-1L) as a white solid.

Next, crude 1-hydroxymethylisourea, i.e., crude compound (1-2L) is obtained from the above-mentioned thin layer chromatography and purified with the use of a cation exchange resin as described above to thereby give the compound (1-2L) as a white solid.

To synthesize the compounds (1-1D) and (1-2D), the above-mentioned procedure is repeated but substituting the compound (a) with the following stereoisomer (ad) (synthesized by the method described in J. Chem. Soc. Perkin Trans. 1, 1992, 1939–1942). Thus the compounds (1-1D) and (1-2D) can be obtained respectively by the procedures of the schemes 1 and 2.

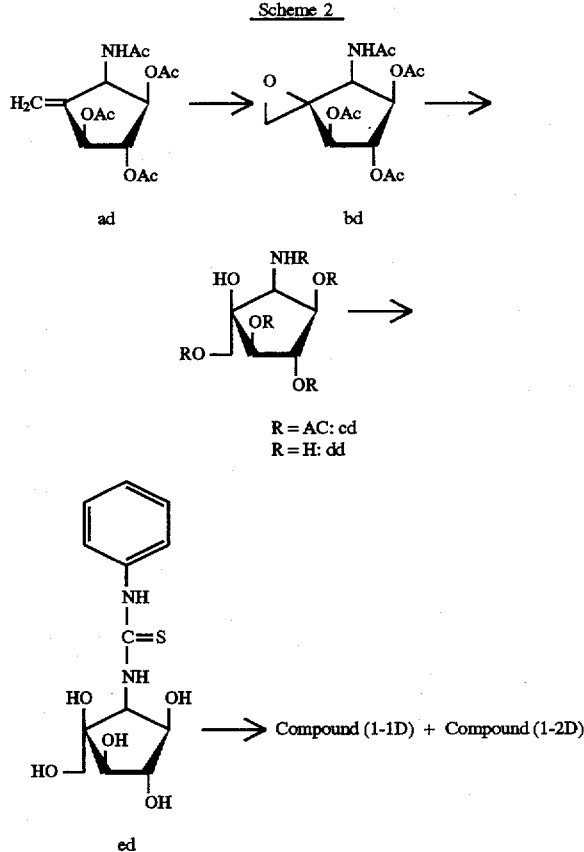

In the schemes 1 and 2, the compound (e) or (ed) having a phenyl group as R$_3$ in the formula (1) is synthesized by reacting the compound (d) or (dd) with phenyl isothiocyanate. In the same manner, a thiourea compound having a different R$_3$ can be obtained by using an isothiocyanate derivative wherein the phenyl group of phenyl isothiocyanate has been substituted with a desired substituent (R$_3$). Then this thiourea compound is converted into a cyclic isourea by the same method as described above and purified. Thus a desired aminocyclopentane derivative of the present invention can be obtained. In other words, the compounds (2-1L), (2-2L), (2-1D) and (2-2D) can be obtained by repeating the above-mentioned procedures but substituting the phenyl isothiocyanate with butyl isothiocyanate.

In the aminocyclopentane derivative of the present invention represented by the formula (2) [hereinafter referred to simply as the compound (2)], $R_4$ and $R_5$ independently represent each H or a substituted or unsubstituted aryl group or an alkyl, alkenyl, alkynyl, hydroxyalkyl group having 1 to 10 carbon atoms. Examples of the substituents of the aryl group include alkyl, alkenyl and alkynyl groups having 1 to 6 carbon atoms, halogen atoms and hydroxyl, nitro and carboxyl groups.

Preferable examples of the compound (2) of the present invention include the compouds (d), (d-1) and (d-2).

The compounds (d-1) and (d-2) of the present invention can be synthesized as follows. The compound (d) is dissolved in an aqueous solution of an alcohol, if necessary, molecular sieve and the like may be added thereto followed by stirring the mixture at 4° to 40° C. for 0.5 to 5 hours. Then butanal is added thereto in 1 to 10 equivalent amount, preferably an equivalent amount, to the compound (d). After stirring at 0° C. to about the boiling point of the reaction mixture (under reflux) for 0.5 to 5 hours, a reducing agent, such as sodium cyanoborohydride, is added thereto in 1 to 10 equivalent amount to the compound (d) and the mixture is stirred at 0° C. to about the boiling point of the reaction mixture (under reflux) for 1 to 72 hours. The reaction system is filtered through celite, etc. and washed with methanol, etc. The filtrate is combined with the washing liquor and concentrated under reduced pressure. The residue thus obtained is subjected to thin layer chromatography, etc. Thus the crude compound (d-1) is first obtained. This crude product is purified with the use of a cation exchange resin as described above to thereby give the compound (d-1).

Next, the crude compound (d-2) is obtained from the above-mentioned thin layer chromatography and purified with the use of a cation exchange resin as described above to thereby give the compound (d-2).

By reacting the compound (d) with butanal, the compound of the formula (2) wherein $R_4$ and/or $R_5$ are butyl groups is prepared. Similarly, a desired aminocyclopentane derivative of the present invention can be obtained by using an aldehyde derivative wherein the butyl group of butanal has been substituted with a desired substituent.

It is expected that the aminocyclopentane derivatives of the present invention, in particular, the compounds (1-1), (1-2) (2-1) and (2-2), which are novel compounds having an endo nitrogen similar to DJN and an exo nitrogen similar to mannostatin, are applicable to novel drugs and agricultural chemicals. It is moreover expected that various analogues can be synthesized from the novel compounds of the present invention to thereby give derivatives of improved specificities.

Hence, the compounds of the present invention can contribute to investigations on systems which seemingly affect various biochemical interactions relating to glucosidase inhibitory activities. Thus these compounds are applicable to the development of novel drugs, for example, antiviral agents such as anti-HIV agents, remedies for diseases relating to the metabolism of saccharides and lipids (for example, obesity, diabetes and mellitus), drugs regulating immune systems such as immunological adjuvants, cancer metastasis suppressors, agricultural chemicals against stripe (caused by *Pellicularia sasakii, Rhizotonia solani*, etc.), antibacterial agents and insecticides. Because of having anti-HIV activities, furthermore, the compounds of the present invention are useful as an anti-HIV agent.

To further illustrate the present invention in greater detail, and not by way of limitation, the following Examples will be given.

The procedures, measuring methods and samples employed in the following Examples are as follows.

Synthesis

1) Thin Layer Chromatography (TLC)

Silica gel for chromatography (Kieselgel 60GF 254, manufactured by Merck & Co., Inc.) was applied onto a glass plate and activated at 70° C. for 30 minutes. Coloration was induced by spraying conc. sulfuric acid onto the plate followed by heating. Ultraviolet absorption measurement was performed by using an UV lamp (254 nm, manufactured by Hirai Rika Kenkyusho) before spraying conc. sulfuric acid.

2) Specific Rotation ($[\alpha]_D$)

A digital polarimeter (DIP-370, manufactured by Nippon Bunko-sha) was used. The measurement was carried out with sodium D ray with the use of a quart cell (10×10 mm).

3) Nuclear Magnetic Resonance Spectrum ($^1$H-NMR, $^{13}$C-NMR)

In the $^1$H-NMR measurement, an NMR spectrometer (JNM-270 FT, 270 MHz, manufactured by JEOL Ltd.) was used. Heavy chloroform or heavy water was employed as a solvent while tetramethylsilane ($\delta 0.00$) (in the case of heavy chloroform) or acetone ($\delta 2.08$) (in the case of heavy water) was employed as an internal reference.

In the $^{13}$C-NMR measurement, an NMR spectrometer (JNM-400 FT, manufactured by JEOL Ltd.) was used. Heavy methanol was used as a solvent while tetramethylsilane ($\delta 0.00$) was employed as an internal reference.

4) Infrared Absorption Spectrum (IR)

In the case of the adhesion method (neat), a sample was adhered to a KBr crystal plate and measured with the use of an infrared spectrometer (Model IR-810, manufactured by Nippon Bunko-sha). In the case of the tablet method (KBr-disk), the measurement was carried out by using a Hitachi 225 diffraction grating BIO-RAD DIGITAL FTS-65 Fourier transform infrared spectrometer.

5) Mass Spectrometry

In the HR-FAB-MS, JEOL JMS HX-110 (manufactured by JEOL, Ltd.) was used. The ion detection mode was FAB Positive and glycerol (cluster ion $[93+(92)_n]^+$) was used as the matrix. As a sample for mass calibration, cesium iodide (CsI) was employed.

6) Preparative Thin Layer Chromatography (PTLC)

A plate for preparative thin layer chromatography (Merck Art 5744, manufactured by Merck & Co., Inc.) was used. Elution was carried out by using methanol.

7) Silica Gel Column Chromatography

Wakogel C-300 (200–300 mesh, manufactured by Wako Pure Chemical Industries, Ltd.) was used.

8) Concentration Under Reduced Pressure

Concentration under reduced pressure was performed under reducing pressure with an aspirator by using a rotary evaporator at a temperature of about 40° C.

9) Reaction Solvent

Every solvent employed in the reactions was an undistilled one.

10) Reaction Reagent mCPBA (m-chloroperbenzoic acid) of a purity of 70% was purchased from Tokyo Kasei.

Sodium acetate was purchased from Wako Pure Chemical Industries, Ltd.

Phenyl isochiocyanate was purchased from Tokyo Kasei.

Mercury oxide was prepared from sodium hydroxide and mercury (II) chloride.

These marketed reagents were used as such.

Enzyme Inhibition Assay

1) Absorbance

By using a 96-well microplate, the absorbance (at 405 nm) of liberated p- or o-nitrophenol was measured with a microplate reader (MPR-4Ai, manufactured by Tosoh Corporation).

2) Incubation

Incubation was carried out at 37° C. by using a natural incubator (Compact NIB-10, manufactured by Iwaki Glass Co., Ltd.).

3) Enzyme

The enzymes employed herein [α-glucosidase (Baker's yeast), β-glucosidase (Almonds), α-galactosidase (*E. coli*), β-galactosidase (*E. coli*) and β-galactosidase (Bovine Liver)] were all purchased from Sigma.

4) Substrate

The substrates (p- or o-nitrophenylglycoside) of these enzymes were all purchased from Sigma.

EXAMPLE 1

Synthesis of (3S,4R,5S,6R,7S)-7-acetamide-4,5,6-tri-O-acetyl-1-oxaspiro[2.4]heptane-4,5,6-triol (compound (b))

The compound (a) (21.7 mg, 0.0725 mmol) was dissolved in 1,2-dichloroethane (2 ml). In the presence of a phosphate buffer solution, 70% mCPBA (53.4 mg, 0.218 mmol, 3 equiv.) was added thereto at room temperature. After stirring in dark for 26 hours, the reaction system was diluted with chloroform (30 ml) and washed successively with a saturated aqueous solution of sodium thiosulfate (5 ml) and a saturated aqueous solution of sodium hydrogencarbonate (5 ml). The organic layer was dried over mirabilite and filtered. The filtrate was concentrated under reduced pressure and the residue thus obtained was purified by silica gel column chromatography (Wakogel C-300, 1 g, acetone/toluene=1/2). Thus the compound (b) (19.8 mg, yield: 86.5%) was obtained as a syrup.

Rf 0.41 (ethanol/toluene=1/5, double development).

$[\alpha]_D^{27}$ −63.7° (c 0.96, chloroform).

IR (neat) 3360 (OH and NH), 1740 (OAc) and 1670 (NAc) cm$^{-1}$.

$^1$H-NMR (270 MHz, CDCl$_3$) δ5.59 (1H, d, $J_{7,NH}$ 9.2 Hz, NH), 5.26 (1H, dd, $J_{4,5}$~1, $J_{5,6}$ 2.9 Hz, 5-H), 5.21–5.17 (2H, m, 4 and 6-H), 5.00 (1H, dd, $J_{6,7}$ 5.1, $J_{7,NH}$ 9.2 Hz, 7-H), 2.98 and 2.68 (each 1H, ABq, $J_{gem}$ 4.8 Hz, 2×2-H), 2.14, 2.12, 2.09 and 2.00 (each 3H, 4s, 4Ac ).

Elemental analysis as C$_{14}$H$_{19}$NO$_8$: calcd.(%): C 51.06, H 5.82, N 4.25 found (%): C 51.61, H 5.82, N 4.20.

EXAMPLE 2

Synthesis of 1L-(1,2,4,5/3)-5-amino-1-hydroxymethyl-1,2,3,4-cyclopentanetetraol (compound (d))

The compound (b) (19.8 mg, 0.0628 mmol) was dissolved in a 80% aqueous solution of DMF (1 ml) and sodium acetate (30.9 mg, 0.377 mmol, 6 equiv.) was added thereto. After stirring at 120° C. for 20 hours, the reaction mixture was concentrated under reduced pressure. The residue thus obtained was acetylated with pyridine (1 ml) and acetic anhydride (0.5 ml). The resulting product was purified by silica gel column chromatography (Wakogel C-300 1 g, acetone/toluene=1/2) to thereby give pentaacetate (compound (c)) (16.0 mg, yield: 65.3%) as a syrup.

The data of the compound (c) agreed with those described in a literature (C. Uchida, T. Yamagishi and S. Ogawa, J. Chem. Soc., Perkin Trans, 1, 1994, 589–602).

The compound (c) (42.5 mg, 0.109 mmol) was dissolved in 2M hydrochloric acid. Then the solution was stirred at 80° C. for 2 hours and concentrated under reduced pressure. The residue thus obtained was purified by using Dowex 50W-X2 (H$^+$, 1 ml, 1M aqueous ammonia) to thereby give epitrehasolamine (compound (d)) (19.7 mg, yield: up to 100%) as a syrup.

Rf 0.38 (water/acetonitrile=1/4).

$[\alpha]_D^{23}$ −3.8° (C 0.98, water).

IR (neat) 3350 (OH and NH$_2$) cm$^{-1}$.

$^1$H-NMR (270 MHz, D$_2$O, ref. acetone) δ3.96 (1H, dd, $J_{2,3}$ 8.1, $J_{3,4}$ 4.8 Hz, 3-H), 3.87 (1H, dd, $J_{3,4}$ 4.8, $J_{4,5}$ 7.7 Hz, 4-H), 3.69 (1H, d, $J_{2,3}$ 8.1 Hz, 2-H), 3.51 (2H, s, 2×6-H), 3.27 (1H, d, $J_{4,5}$ 7.7 Hz, 5-H).

EXAMPLE 3

Synthesis of N-[(1R)-(1,2,3,5/4)-2-hydroxymethyl-2,3,4,5-tetrahydroxycyclopentyl]-N'-phenylthiourea (compound (e))

The compound (d) (15.3 mg, 0.0854 mmol) was dissolved in a 60% aqueous solution of ethanol (1 ml) and phenyl isothiocyanate (23 μl, 0.171 mmol, 2.0 equiv.) was added thereto. After stirring for 3 hours, the reaction mixture was concentrated under reduced pressure and the resulting residue was purified by silica gel column chromatography (Wakogel C-300, 2 g, toluene—ethanol/toluene=1/5) to thereby give the phenylthiourea compound, i.e., the compound (e) (23.6 mg, yield: 88.1%) as a white solid.

Rf 0.41 (ethanol/toluene=1/2).

$[\alpha]_D^{22}$ +43.9° (c 1.18, acetone).

IR (KBr disk) 3280 (OH and NH) and 1540 (NH) cm$^{-1}$.

$^1$H-NMR (270 MHz, D$_2$O, ref. acetone) δ7.38–7.17 (5H, m, Ph), 4.66 (1H, m, 1-H), 3.97 (1H, dd, $J_{1,5}$ 8.1, $J_{4,5}$ 4.6 Hz, 5-H), 3.87 (1H, dd, $J_{3,4}$ 8.4, $J_{4,5}$ 4.6 Hz, 4-H), 3.67 (1H, d, $J_{3,4}$ 8.4 Hz, 3-H), 3.38 and 3.33 (each 1H, ABq, $J_{gem}$ 12.1 Hz, 2×6-H).

Elemental analysis as C$_{13}$H$_{18}$N$_2$O$_5$S: calcd.(%): C 49.67, H 5.77, N 8.91 found (%): C 49.93, H 6.17, N 8.59.

EXAMPLE 4

Synthesis of (1S,5R,6S,7S,8R)-6-hydroxymethyl-3-phenylamino-2-oxa-4-azabicyclo[3.3.0]oct-3-ene-6,7,8-triol [compound (1-1L)] and (1S,5R,6S,7R,8S)-1-hydroxymethyl-3-phenylamino-2-oxa-4-azabicyclo[3.3.0]oct-3-ene-6,7,8-triol [compound (1-2L)]

The compound (e) (23.6 mg, 0.0751 mmol) was dissolved in acetone/ethanol (1.5 ml, v/v) and mercury oxide (yellow) (55.2 mg, 0.256 mmol, 3 equiv.) was added thereto. After stirring at room temperature for 2 hours, the reaction system was filtered through celite and thoroughly washed with methanol. The filtrate was combined with the washing liquor and concentrated under reduced pressure. The residue thus obtained was separated by PTLC (acetic acid/ethanol/toluene=1/2/4, 4 time-development). Thus crude 6-hydroxymethylisourea [compound (1-1L)] was first obtained. Then it was purified by using Dowex 50W-X2 (H$^+$, 1 ml, 14M aqueous ammonia:methanol=1/28) to thereby give the compound (1-1L) (9.2 mg, yield: 43.8%) as a white solid.

Rf 0.22 (ethanol/toluene=1/2).

$[\alpha]_D^{28}$ +50.1° (c 0.15, methanol).

IR (KBr disk) 3430 (OH and NH), 1660 (C=N) and 1580 (NH) cm$^{-1}$.

$^1$H-NMR (270 MHz, D$_2$O, ref. acetone) δ7.26–6.97 (5H, m, Ph), 4.56 (1H, dd, J$_{1,5}$ 9.5, J$_{1,8}$ 4.2 Hz, 1-H), 4.25 (1H, d, J$_{1,5}$ 9.5 Hz, 5-H), 4.13 (1H, dd, J$_{1,8}$ 4.2, J$_{7,8}$ 9.5 Hz, 8-H), 3.67 (1H, d, J$_{7,8}$ 9.5 Hz, 7-H), 3.46 (2H, s, 2×9-H).

Elemental analysis as C$_{13}$H$_{16}$N$_2$O$_5$: calcd.(%): C 55.71, H 5.75, N 9.99 found (%): C 55.30, H 5.81, N 9.84.

Next, crude 1-hydroxymethylisourea [compound (1-2L)] was obtained and purified by using Dowex 50W-X2 (H$^+$, 1 ml, 14M aqueous ammonia: 50% aqueous solution of methanol=1/28) to thereby give the compound (1-2L) (10.6 mg, yield: 50.5%) as a white solid.

Rf 0.17 (ethanol/toluene=1/2).

$[\alpha]_D^{28}$ −27.5° (c 0.26, methanol).

IR (KBr disk) 3420 (OH and NH), 1670 (C=N) and 1560 (NH) cm$^{-1}$.

$^1$H-NMR (270 MHz, D$_2$O, ref. acetone) δ7.29–6.97 (5H, m, Ph), 4.06 (1H, d, J$_{5,6}$ 5.9 Hz, 5-H), 3.76 and 3.56 (each 1H, ABq, J$_{gem}$ 12.5 Hz, 2×9-H), 3.72–3.61 (3H, m, 6, 7 and 8-H).

Elemental analysis as C$_{13}$H$_{16}$N$_2$O$_5$: calcd.(%): C 55.71, H 5.75, N 9.99 found (%): C 55.25, H 5.75, N 10.01.

EXAMPLE 5

By repeating the procedures of the above Examples 1 to 4, the compounds (1-1D) and (1-2D) were obtained in accordance with the scheme 2.

EXAMPLE 6

Synthesis of N-[(1R)-(1,2,3,5/4)-2-hydroxymethyl-2,3,4,5-tetrahydroxycyclopentyl]-N'-butylthiourea Butyl isothiocyanate was prepared in the following manner in accordance with the method of Furukawa et al. [Nippon Kagaku Kaishi (1989), p. 822–825]. Triphenylphosphine (31.47 g, 0.12 mol) was dissolved in benzene (20 ml) and triethylamine (41.8 ml, 0.30 mol) and carbon disulfide (7.3 ml, 0.12 mol) were added thereto. After adding acetonitrile (150 ml), the reaction system was cooled to −15° C. and butylamine (9.9 ml, 0.10 mol) and carbon tetrachloride (9.7 ml, 0.10 mol) were added thereto followed by stirring. After 30 minutes, the reaction system was heated to 0° C. and stirred for 1 hour. Then the reaction mixture was further heated to room temperature and stirred for 5 hours. The reaction mixture was filtered and the insoluble matters were eliminated. Then the filtrate was concentrated to about 50 ml under reduced pressure and extracted with hexane (100 ml×5). The organic layers were combined and dried over mirabilite. After repeating filtration and concentration under reduced pressure, the resulting liquid residue was purified by distillation under reduced pressure. Thus butyl isothiocyanate (6.34 g, yield: 55.0%) was obtained as a liquid.

b.p.: 75°–76° C. (31 mmHg) [reported in the literature cited above: 76°–77° C. (22 mmHg)].

The compound (d) (epitrehasolamine) (21.4 mg, 0.119 mmol) was dissolved in a 60% aqueous solution of ethanol (1.5 ml). Then the above-mentioned butyl isothiocyanate (44 μl, 0.358 mmol, 3 equiv.) prepared from butylamine was added thereto and the resulting mixture was stirred at room temperature. 3, 5 and 19 hours thereafter, butyl isothiocyanate was added each in the same amount (i.e., 4 times in total, 176 ml, 1.43 mmol, 12 equiv.) and the mixture was stirred for 22 hours. The reaction mixture was concentrated under reduced pressure and the resulting residue was purified by silica gel column chromatography [Katayama 60 (trade name, marketed from Katayama Chemical), 8 g, ethanol/toluene=1/3] to thereby give a butylthiourea compound (35.2 mg, yield: up to 100%) as a white solid.

Rf 0.36 (ethanol/toluene=1/2).

$[\alpha]_D^{21}$ +38.1° (c2.06, methanol).

IR (KBr disk) 3370 (OH and NH) and 1560 (NH) cm$^{-1}$.

$^1$H-NMR (270 MHz, D$_2$O, ref. acetone) δ4.70–4.60 (1H, m, 1-H), 3.95–3.87 (2H, m, 4 and 5-H), 3.67 (1H, d, J$_{3,4}$ 8.4 Hz, 3-H), 3,40–3.25 (2H, m, NC$\underline{H}_2$CH$_2$CH$_2$CH$_3$), 3.37 and 3.30 (each 1H, ABq, J$_{gem}$ 11.9 Hz, 2×6-H), 1.49–1.37 (2H, m, NCH$_2$C$\underline{H}_2$CH$_2$CH$_3$), 1.29–1.14 (2H, m, NCH$_2$CH$_2$C$\underline{H}_2$CH$_3$), 0.76 (3H, t, J$_{3',4'}$ 7.3 Hz, NCH$_2$CH$_2$CH$_2$C$\underline{H}_3$).

Elemental analysis as C$_{11}$H$_{22}$N$_2$O$_5$S: calcd.(%): C 44.88, H 7.53, N 9.52 found (%): C 44.26, H 7.94, N 9.38.

EXAMPLE 7

Synthesis of (1S,5R,6S,7S,8R)-6-hydroxymethyl-3-butylamino-2-oxa-4-azabicyclo[3.3.0]oct-3-ene-6,7,8-triol [compound (2-1L)] and (1S,5R,6S,7R,8S)-1-hydroxymethyl-3-butylamino-2-oxa-4-azabicyclo[3.3.0]oct-3-ene-6,7,8-triol [compound (2-2L)]

The butylthiourea compound (35.2 mg, 0.119 mmol) obtained in Example 6 was dissolved in acetone/ethanol (2 ml, 1/1, v/v) and mercury oxide (77.0 mg, 0.357 mmol, 3 equiv.) was added thereto. The resulting mixture was stirred at room temperature. After 6 hours, the same amount (77 mg) of mercury oxide was further added and the mixture was stirred for additional 3 hours. Then the reaction system was filtered through celite and thoroughly washed with methanol. The filtrate was combined with the washing liquor and concentrated under reduced pressure. The resulting residue was separated by silica gel column chromatography [Katayama 60 (trade name, marketed from Katayama Chemical), 8 g, acetic acid/ethanol/toluene=1/2/4]. Thus crude 6-hydroxymethylisourea [compound (2-1L)] was first obtained and purified with the use of Dowex 50W-X2 (H$^+$, 1 ml, 14M aqueous ammonia:methanol=1/28) to thereby give the compound (2-1L) (8.4 mg, yield: 23.1%) as a white solid.

Rf 0.14 (acetic acid/ethanol/toluene=1/2/4).

$[\alpha]_D^{23}$ +35.2° (c0.41, methanol).

IR (KBr disk) 3400 (OH and NH), 1655 (C=N) and 1555 (NH) cm$^{-1}$.

$^1$H-NMR (270 MHz, D$_2$O, ref. acetone) δ4.45 (1H, dd, J$_{1,5}$ 9.2, J$_{1,8}$ 4.4 Hz, 1-H), 4.18 (1H, d, J$_{1,5}$ 9.2 Hz, 5-H), 4.02 (1H, dd, J$_{1,8}$ 4.4, J$_{7,8}$ 9.7 Hz, 8-H), 3.63 (1H, d, J$_{7,8}$ 9.7 Hz, 7-H), 3.44 and 3.39 (each 1H, ABq, J$_{gem}$ 11.7 Hz, 2×9-H), 3.01 (2H, t, J$_{1',2'}$ 7.0 Hz, NC$\underline{H}_2$CH$_2$CH$_2$CH$_3$), 1.41–1.31 (2H, m, NCH$_2$C$\underline{H}_2$CH$_2$CH$_3$), 1.25–1.11 (2H, m, NCH$_2$CH$_2$C$\underline{H}_2$CH$_3$), 0.74 (3H, t, J$_{a',4'}$ 7.3 Hz, NCH$_2$CH$_2$CH$_2$C$\underline{H}_3$).

$^{13}$C-NMR (100 MHz, CD$_3$OD, ref. TMS) δ164.89, 87.34, 82.24, 78.57, 77.19, 67.78, 64.23, 43.47, 32.83, 21.01, 14.16.

Elemental analysis as C$_{11}$H$_{20}$N$_2$O$_5$: calcd. (%): C 50.76, H 7.74, N 10.76 found (%): C 50.35, H 8.09, N 10.46.

Next, crude 1-hydroxymethylisourea [compound (2-2L)] was obtained and purified with the use of Dowex 50W-X2

(H⁺, 1 ml, 14M aqueous ammonia: 50% aqueous solution of methanol=1/28) to thereby give the compound (2-2L) (11.7 mg, yield: 32.1%) as a white solid.

Rf 0.12 (acetic acid/ethanol/toluene=1/2/4).

$[\alpha]_D^{23}$ +16.7° (C0.58, methanol).

IR (KBr disk) 3400 (OH and NH), 1660 (C=N) and 1560 (NH) cm⁻¹.

¹H-NMR (270 MHz, D₂O, ref. acetone) δ3.97 (1H, d, $J_{1,5}$ 6.2 Hz, 5-H), 3.68 and 3.49 (each 1H, ABq, $J_{gem}$ 12.5 Hz, 2×9-H), 3.64–3.54 (3H, m, 6, 7 and 8-H), 3.02 (2H, t, $J_{1',2'}$ 6.8 Hz, NC$\underline{H}_2$CH₂CH₂CH₃), 1.42–1.32 (2H, m, NCH₂C$\underline{H}_2$CH₂CH₃), 1.26–1.02 (2H, m, NCH₂CH₂C$\underline{H}_2$CH₃), 0.74 (3H, t, $J_{3',4'}$ 7.1 Hz, NCH₂CH₂CH₂C$\underline{H}_3$).

¹³C-NMR (100 MHz, CD₃OD, ref. TMS) δ163.59, 91.02, 80.12, 75.90, 75.16, 68.78, 63.31, 43.49, 32.86, 21.05, 14.19.

Elemental analysis as C₁₁H₂₀N₂O₅: calcd.(%): C 50.76, H 7.74, N 10.76 found (%): C 50.41, H 8.16, N 10.61.

EXAMPLE 8

Synthesis of 1L-(1,2,4,5/3)-5-dibutylamino-1-hydroxymethyl-1,2,3,4-cyclopentanetetraol [compound (d-1)] and 1L-(1,2,4,5/3)-5-butylamino-1-hydroxymethyl-1,2,3,4-cyclopentanetetraol [compound (d-2)]

The compound (c) (epitorehasolamine pentaacetate; 51.8 mg, 0.1331 mmol) was dissolved in 2M hydrochloric acid (2 ml) and stirred at 80° C. for 2 hours. After cooling to the room temperature, the reaction system was concentrated under reduced pressure to thereby give epitrehasolamine hydrochloride as the residue. Then this residue was dissolved in methanol (1.5 ml) and Molecular Sieves 4A (50.0 mg) was added thereto. After stirring at room temperature for 2 hours, butanal (13.2 μl, 0.1464 mmol, 1.1 equiv.) was added thereto and the resulting mixture was stirred at room temperature for additional 1 hour. Next, sodium cyanoborohydride (26.4 mg, 0.3992 mmol, 3 equiv.) was added thereto and the mixture was stirred at the same temperature for 3 hours. The reaction system was filtered through celite and thoroughly washed with methanol. Then the filtrate was concentrated under reduced pressure and the residue thus obtained was separated by silica gel column chromatography (Wakogel C-300, 2 g, acetic acid/methanol/chloroform= 1/4/12). Thus crude dibutyl epitrehasolamine [compound (d-1)] was first obtained. This crude product was further adsorbed by Dowex 50W-X2 (H⁺, 1 ml), thoroughly washed with water and eluted with 14M aqueous ammonia/methanol (1:13) to thereby give the compound (d-1) (4.2 mg, yield: 10.9%) as a syrup.

Rf 0.47 (12M hydrochloric acid/acetonitrile=1/8).

$[\alpha]_D^{23}$ −18.5° (c0.21, methanol).

IR (KBr disk) 3400 (OH and NH), 1620 (NH) cm⁻¹.

¹H-NMR (270 MHz, D₂O, ref. acetone) δ3.95 (1H, dd, $J_{3,4}$ 4.4, $J_{4,5}$ 6.4 Hz, 4-H), 3.89 (1H, dd, $J_{2,3}$ 6.0, $J_{3,4}$ 4.4 Hz, 3-H), 3.53 (1H, d, $J_{2,3}$ 6.0 Hz, 2-H), 3.49 and 3.43 (each 1H, ABq, $J_{gem}$ 11.7 Hz, 2×6-H), 3.06 (1H, d, $J_{4,5}$ 6.4 Hz, 5-H), 2.83–2.65 (4H, m, NC$\underline{H}_2$CH₂CH₂CH₃), 1.42–1.28 (4H, m, NCH₂C$\underline{H}_2$CH₂CH₃), 1.22–1.08 (4H, m, NCH₂CH₂C$\underline{H}_2$CH₃), 0.76 (6H, t, $J_{3',4'}$ 7.1 Hz, NCH₂CH₂CH₂C$\underline{H}_3$).

¹³C-NMR (100 MHz, CD₃OD, ref. TMS) δ84.77, 80.28, 78.84, 78.20, 67.12, 64.05, 53.33 (2C), 31.70 (2C), 21.58 (2C), 14.50 (2C).

HR-FAB-MS [M+H]⁺ found: 292.2124 calcd.: 292.2124.

Next, crude monobutyl epitrehasolamine [compound (d-2)] was obtained and purified with the use of Dowex 50W-X2 (H⁺, 1 ml) in the same manner as the one employed in the case of the dibutyl compound to thereby give the compound (d-2) (4.6 mg, yield: 14.7% ) as a syrup.

Rf 0.43 (12M hydrochloric acid/acetonitrile=1/8).

$[\alpha]_D^{23}$ +10.9° (C0.23, methanol).

IR (KBr disk) 3350 (OH and N) cm⁻¹.

¹H-NMR (270 MHz, D₂O, ref. acetone) δ3.84 (1H, dd, $J_{3,4}$ 4.8, $J_{4,5}$ 7.3 Hz, 4-H), 3.78 (1H, dd, $J_{2,3}$ 7.7, $J_{3,4}$ 4.8 Hz, 3-H), 3.54 (1H, d, $J_{2,3}$ 7.7 Hz, 2-H), 3.42 and 3.38 (each 1H, ABq, $J_{gem}$ 12.3 Hz, 2×6-H), 2.94 (1H, d, $J_{4,5}$ 7.3 Hz, 5-H), 2.59–2.41 (2H, m, NC$\underline{H}_2$CH₂CH₂CH₃), 1.39–1.26 (2H, m, NCH₂C$\underline{H}_2$CH₂CH₃), 1.23–1.12 (2H, m, NCH₂CH₂C$\underline{H}_2$CH₃), 0.75 (3H, t, $J_{3',4'}$ 7.1 Hz, NCH₂CH₂CH₂C$\underline{H}_3$).

¹³C-NMR (100 MHz, CD₃OD, ref. TMS) δ83.25, 77.93, 76.85, 74.27, 65.76, 60.75, 53.29, 33.32 21.40, 14.32.

HR-FAB-MS [M+H]⁺ found: 236.1492. calcd.: 236.1498.

TEST EXAMPLE 1

The inhibitory activities on the following enzymes were examined by using the compounds (d), (d-1), (d-2), (1-1L), (1-D), (1-2L), (1-2D) and (2-2L) obtained in the above Examples, deoxynojirimycin (DNJ), N-butyldeoxynojirimycin (referred to as N-B-DNJ) and trehasolamine as samples.

1) α-Glucosidase (Baker's yeast, EC 3.2.1.20) [described in H. Halvorson and L. Ellias, Biochim. Biophys. Acta, 30, 28–40 (1958)]

Into each well were introduced an aqueous solution of a sample (1 μl), a 0.66 mM solution of p-nitrophenyl α-D-glucopyranoside in a buffer (98 μl) and a (0.4 mg/ml) enzyme solution in the buffer (1 μl) to give a total volume of 100 μl. After incubating at 37° C. for 30 minutes, the reaction was ceased by adding a 1M aqueous solution of sodium carbonate (100 μl). Then the absorbance ($A_{405}$) of p-nitrophenol liberated by this enzyme reaction was measured. To give the blank absorbance ($A_{blank}$), the sample (1 μl) and the substrate (99 μl) were incubated in the same manner and an aqueous solution of sodium carbonate (100 μl) was added followed by the measurement of the absorbance. To give the control absorbance ($A_{control}$), on the other hand, water (1 μl), the substrate (98 μl) and the enzyme solution (1 μl) were incubated in the same manner and an aqueous solution of sodium carbonate (100 μl) was added followed by the measurement of the absorbance. The sample at each concentration, the blank and the control were treated each in two wells at the same time. As the buffer, a 0.1M phosphate buffer solution (pH 6.8, prepared from KH₂PO₄ and K₂HPO₄) was employed.

The 50% inhibitory concentration [IC₅₀ (M)] of the enzyme activity was determined on the basis of the absorbances at sample concentrations diluted successively [i.e., 100, 50, 25, 12.5, 6.25, - - - (μg/μl)].

2) β-Glucosidase (Almonds, EC 3.2.1.21) [described in A. Kobayashi, Agr. Biol. Chem., 26, 203–207 (1962)]

Into each well were introduced an aqueous solution of a sample (1 μl), a 0.33 mM solution of p-nitrophenyl β-D-glucopyranoside in a buffer (98 μl) and a (0.4 mg/ml) enzyme solution in the buffer (1 μl) to give a total volume of 100 μl. After incubating at 37° C. for 45 minutes, the reaction was ceased by adding a 1M aqueous solution of sodium carbonate (100 μl). Then the absorbance ($A_{405}$) of p-nitrophenol liberated by this enzyme reaction was measured. To give the blank absorbance ($A_{blank}$), the sample (1

μl) and the substrate (99 μl) were incubated in the same manner and an aqueous solution of sodium carbonate (100 μl) was added followed by the measurement of the absorbance. To give the control absorbance ($A_{control}$), on the other hand, water (1 μl), the substrate (98 μl) and the enzyme solution (1 μl) were incubated in the same manner and an aqueous solution of sodium carbonate (100 μl) was added followed by the measurement of the absorbance. As the buffer, a 0.1M acetate buffer solution (pH 5.0, prepared from NaOAc and AcOH) was employed. The $IC_{50}$ was determined in the same manner as employed in the case of α-glucosidase.

3) α-Galactosidase (E. Coli, EC. 3.2.1.22) [described in H. Suzuki, S-C. Li and Y-T. Li, J. Biol. Chem., 245, 781–786 (1970)]

Into each well were introduced an aqueous solution of a sample (1 μl), a buffer (74 μl), a 9.9 mM solution of p-nitrophenyl α-D-galactopyranoside in a buffer (20 μl) and a (50 μg/ml) enzyme solution in the buffer (5 μl) to give a total volume of 100 μl. After incubating the resulting mixture at room temperature (20°–30° C.) for 15 minutes, the reaction was ceased by adding a 0.2M borate buffer solution (pH 9.8, prepared from NaOH and $H_3BO_3$, 100 μl). Then the absorbance ($A_{405}$) of p-nitrophenol liberated by this enzyme reaction was measured. To give the blank absorbance ($A_{blank}$), the sample (1 μl), the substrate (20 μl) and the buffer solution (79 μl) were incubated in the same manner and the 0.2M borate buffer solution (100 μl) was added followed by the measurement of the absorbance. To give the control absorbance ($A_{blank}$), on the other hand, water (1 μl), the substrate (20 μl), the buffer solution (74 μl) and the enzyme solution (5 μl) were incubated in the same manner and the borate buffer solution (100 μl) was added followed by the measurement of the absorbance. A 0.1M phosphate buffer solution (pH 6.5, prepared from $KH_2PO_4$ and $K_2HPO_4$) was employed as the buffer for the enzyme reaction. The $IC_{50}$ was determined in the same manner as employed in the case of α-glucosidase.

4) β-Galactosidase (E. Coli, EC. 3.2.1.23) [described in G. R. Craven, E. Steers, Jr. and C. B. Anfinsen, J. Biol. Chem., 240, 2468–2477 (1965)]

Into each well were introduced an aqueous solution of a sample (2 μl), a buffer (153 μl), a 20 mM solution of o-nitrophenyl β-D-galactopyranoside in a buffer (25 μl), a 100 mM 2-mercaptoethanol (10 μl) and a (10 μg/ml) enzyme solution in the buffer (10 μl) to give a total volume of 200 μl. After incubating at room temperature (20°–30° C.) for 30 minutes, the absorbance ($A_{405}$) of o-nitrophenol liberated by this enzyme reaction was measured. To give the blank absorbance ($A_{blank}$), the sample (2 μl), the substrate (25 μl), the buffer solution (163 μl) and 2-mercaptoethanol (10 μl) were incubated in the same manner followed by the measurement of the absorbance. To give the control absorbance ($A_{control}$), on the other hand, water (2 μl), the substrate (25 μl), the buffer solution (153 μl), 2-mercaptoethanol (10 μl) and the enzyme solution (10 μl) were incubated in the same manner followed by the measurement of the absorbance. A 50 mM phosphate buffer solution (pH 7.3, prepared from $KH_2PO_4$ and $K_2HPO_4$, containing 1.3 mM of $MgCl_2$) was employed as the buffer for the enzyme reaction. The $IC_{50}$ was determined in the same manner as employed in the case of α-glucosidase.

5) β-Galactosidase (Bovine liver. EC 3.2.1.23) [described in T. Aoyagi, T. Hazato, M. Kumagai, M. Hamada, T. Takeuchi and H. Umezawa, J. Antibiot., 28, 1006–1008 (1975)]

Into each well were introduced an aqueous solution of a sample (2 μl), a buffer (158 μl), a 20 mM solution of o-nitrophenyl β-D-galactopyranoside in a buffer (25 μl), a 100 mM 2-mercaptoethanol (10 μl) and a (5 mg/ml) enzyme solution in the buffer (5 μl) to give a total volume of 200 μl. After incubating at room temperature (20°–30° C.) for 30 minutes, the absorbance ($A_{405}$) of o-nitrophenol liberated by this enzyme reaction was measured. To give the blank absorbance ($A_{blank}$), the sample (2 μl), the substrate (25 μl), the buffer solution (163 μl) and 2-mercaptoethanol (10 μl) were incubated in the same manner followed by the measurement of the absorbance. To give the control absorbance ($A_{control}$), on the other hand, water (2 μl), the substrate (25 μl), the buffer solution (158 μl), 2-mercaptoethanol (10 μl) and the enzyme solution (5 μl) were incubated in the same manner followed by the measurement of the absorbance. A 50 mM phosphate buffer solution (pH 7.3, prepared from $KH_2PO_4$ and $K_2HPO_4$, containing 1.3 mM of $MgCl_2$) was employed as the buffer for the enzyme reaction. The $IC_{50}$ was determined in the same manner as the one employed in the case of α-glucosidase.

The results are given in Table 1.

TABLE 1

| | $IC_{50}(M)$ | | | | |
|---|---|---|---|---|---|
| Compound | α-Glucosidase (Baker's yeast) | β-Glucosidase (Almonds) | α-Galactosidase (E. coli) | β-Galactosidase (E. coli) | β-Galactosidase (Bovine Liver) |
| d | $4.02 \times 10^{-7}$ | $2.93 \times 10^{-5}$ | — | — | $3.63 \times 10^{-4}$ |
| 1-1D | $2.32 \times 10^{-6}$ | — | — | — | $3.00 \times 10^{-6}$ |
| 1-1L | $2.93 \times 10^{-8}$ | — | — | — | $1.53 \times 10^{-4}$ |
| 1-2D | $9.99 \times 10^{-7}$ | — | — | — | $1.89 \times 10^{-6}$ |
| 1-2L | $5.0 \times 10^{-12}$ | — | — | — | $5.17 \times 10^{-5}$ |
| 2-2L | $7.0 \times 10^{-14}$ | — | ... | ... | ... |
| d-1 | $5.0 \times 10^{-7}$ | $1.3 \times 10^{-4}$ | ... | ... | ... |
| d-2 | $1.7 \times 10^{-8}$ | $3.0 \times 10^{-6}$ | ... | ... | ... |
| DNJ | $9.19 \times 10^{-5}$ | $1.47 \times 10^{-4}$ | ... | ... | — |
| N-B-DNJ | $8.0 \times 10^{-5}$ | $5.0 \times 10^{-4}$ | ... | ... | ... |
| trehasolamine | $5.0 \times 10^{-4}$ | $9.9 \times 10^{-6}$ | ... | ... | ... |

Note)
—: exceeding $3.0 \times 10^{-4}$M.
...: not measured.

As the above Table shows, the compounds of the present invention including the compounds (d) (epitrehasolamine), (d-1) and (d-2) and five isourea compounds [i.e., compounds (1-1L), (1-1D), (1-2L), (1-2D) and (2-2L)] have α-glucosidase inhibitory activities $10^2$ to $2 \times 10^9$ times as high as that of deoxynojirimycin. It is also shown that these compounds are highly specific to α-glucosidase. Moreover, the above-mentioned five isourea compounds have each a higher inhibitory activity and higher α,β-selectivity respectively than those of epitrehasolamine, which indicates that they are highly useful compounds. A comparison in the inhibitory activity between the compound (1-1L), in which the secondary hydroxyl group participates in the isourea bond, and the compound (1-2L), in which the tertiary hydroxyl group participates in the isourea bond, indicates that the latter compound has a somewhat higher activity. This fact suggests that the hydroxyl group corresponding to the 2-position of glucose might contribute to the hydrogen bond as a proton donor in the binding to the enzyme employed in this study. Furthermore, the α,β-selectivity of the compound (d) can be remarkably elevated by introducing a phenyl group thereinto. Based on this fact, it is assumed that the hydrophobic moiety would largely affect the selectivity.

TEST EXAMPLE 2

The inhibitory activities on α-glucosidase I were examined with the use of the compounds (d), (1-2L) and (2-2L) obtained in Examples and comparative compounds trehasolamine and N-butyl deoxynojirimycin.

The α-glucosidase I (Baker's yeast) and its substrate (α-D-Glcl→2α-D-Glcl→3α-D-Glc-O(CH$_2$)$_6$COOCH$_3$) employed herein were prepared in accordance with the method of I. Neverova et al., Anal. Biochem., 222, 190–196 (1994).

The following measurements were performed by the methods described in this literature.

Namely, 25 μl of a buffer solution containing α-glucosidase I was added to a microtube containing the above-mentioned sample and the substrate (α-D-Glcl→2α-D-Glcl→3α-D-Glc-O(CH$_2$)$_6$COOCH$_3$). After incubating at 37° C. for 1 hour, a 1.25M tris hydrochloride buffer solution (pH 7.6, 25 μl) was added to thereby cease the reaction. Then the reaction mixture was transferred onto a microplate followed by the addition of 250 μl of a reaction buffer solution [developing solution; 1M tris hydrochloride buffer solution (pH 7.2) containing glucose oxidase (5 units/ml, manufactured by Sigma), horseradish peroxidase (1 purpurogallin units, manufactured by Sigma) and o-dianisidine dihydrochloride (40 μg/ml)]. Then the mixture was incubated at 37° C. for 30 minutes or until an increase in the absorbance attained a plateau. Then the absorbance ($A_{450-650}$) of the o-dianisidine formed and oxidized by this enzyme reaction was measured. As a blank, the above reaction was repeated but adding neither the above-mentioned sample nor substrate and the absorbance was measured. Also, the above-mentioned reaction buffer solution was added to D-glucose of a known concentration and the resulting mixture was incubated followed by the measurement of the absorbance to thereby examine a relationship between D-glucose concentration and absorbance. Each measurement was effected in two wells at the same time.

The above-mentioned measurement was carried out within a substrate concentration range (0.25–4.0 mM) and a sample concentration range around the level giving IC$_{50}$ of each sample. Based on the above-mentioned relationship between D-glucose concentration and absorbance, the amount of glucose liberated from the substrate due to the enzyme reaction of α-glucosidase I in the presence of the sample was determined. From the result thus obtained, Km was determined and then Ki was determined from the sample amount and the Km value.

Table 2 shows the results. As Table 2 shows, the compounds of the present invention inhibit the enzyme activity of α-glucosidase I. Among all, the compound (2-2L) is comparable in activity to N-butyl deoxynojirimycin which has been studied and developed as an anti-HIV agent. Thus it is expected that the compound (2-2L) is also usable as an anti-HIV agent.

TABLE 2

| Compound | Ki (μM) |
| --- | --- |
| d | 300 |
| 1-2L | 51 |
| 2-2L | 4.2 |
| N-butyl deoxynojirimycin | 3.6 |
| trehasolamine | 1500 |

TEST EXAMPLE 3

Inhibitory Effect of Aminocyclopentane Derivatives on HIV Production (HIV-neutralization Assay)

The HIV-neutralization activities of the compounds of the present invention were determined by the virus neutralization assay with the use of human normal peripheral blood mononuclear cells (PBMC).

The compounds (d), (1-1L), (1-2L) and (2-2L) obtained in Examples and comparative compounds N-methyl deoxynojirimycin (referred to as N-mDNJ), N-butyl deoxynojirimycin (referred to as N-B-DNJ), trehasolamine and azidothymidine (AZT) were employed as samples each in amounts of 0.1 μM and 1 μM, mixed with HIV$_{MN}$ in an amount 100 times as much as TCID$_{50}$ (median tissue culture infection dose) and then incubated at 37° C. for 60 minutes. The mixture was transferred into an Eppendorf tube containing $1 \times 10^6$ PBMC, which had been activated with 5 μg of phytohemagglutinin (PHA) for 24 hours, and shaken in a water bath at 37° C. for 60 minutes. The activation with PHA was performed by incubating PBMC in a stimulation medium for 24 hours. This stimulation medium was prepared by adding glutamine (2mM), heat-inactivated 10% fetal calf serum, 0.01% PHA (manufactured by Difco), anti-INFα antibody (50 units/ml, marketed from Cosmobio), penicillin (50 units/ml) and streptomycin (50 μg/ml) to RPMI1640 medium. After washing with PBS three times, the cells were suspended in 1 ml of a growth medium. Then, the suspension was transferred into an incubation tube (A-S Nunc, Roskilde, Denmark) and incubated for 7 days. This growth medium was prepared by adding glutamine (2 μM), heat-inactivated 10% fetal calf serum, T cell growth factor (IL-2) (40 units/ml, manufactured by Shionogi & Co., Ltd.), anti-INFα antibody (50 units/ml, marketed from Cosmobio), penicillin (50 units/ml) and streptomycin (50 μg/ml) to RPMI1640 medium. Then the production of HIV in the supernatant was assayed with the use of HIV-1 p24 antigen ELISA (manufactured by Dinabot) [J. Immunol., 142, 4248–4255 (1989); J. Immunol., 148, 2175–2180 (1992)] and the inhibitory effect of a sample on the HIV production was expressed in inhibition ratio (%).

The HIV$_{MN}$ used in the neutralization assay was prepared by incubating PBMC, which had been activated with 5 μg/ml of PHA for 7 days, with HIV$_{MN}$ (H9/HTLV-III$_{MN}$, AIDS Research and Reference Reagent Program, NIH, Rockyill, Md.) in an amount 100 times as much as $TCID_{50}$ for 7 days and eliminating the cells from the culture supernatant followed by preservation at −130 ° C. prior to use. The $HIV_{MN}$ was titrated with PHA-activated PBMC to thereby define $TCID_{50}$ per ml.

FIG. 1 shows the results. The ordinate refers to the degree of inhibition by each specimen which is expressed in the inhibition ratio (%) calculated by regarding the inhibition of 1 μM of AZT as 70%. As FIG. 1 shows, the compounds of the present invention have anti-HIV activities.

TEST EXAMPLE 4

Inhibitory Effect of Aminocyclopentane Derivatives on Cell Fusion (Formation of Giant Cells) Induced by HIV To media containing $10^6$ Molt4 cells or $10^6$ Molt4/HIV-III B cells were respectively added the compounds (1-2L), (2-2L), (d), (d-2) and (d-1) obtained in Examples and comparative compounds N-mDNJ, N-B-DNJ and AZT employed as samples each in amounts of 0.1 μM and 1 μM followed by incubation for 3 days. Each medium employed herein was prepared by adding glutamine (2 mM), heat-inactivated 10% fetal calf serum, penicillin (50 units/ml) and streptomycin (50 mg/ml) to RPMI1640 medium. After the completion of the incubation, the Molt4 cells were mixed with the Molt4/HIV-III B cells in the same number and incubated at 37° C. for 24 hours. Then the cell size and the cell count were measured with the use of a multisizer (manufactured by Coulter). Cells exceeding 20 μm in diameter were referred to as giant cells formed by the cell fusion. Thus the inhibition ratio (%) of each sample on the cell fusion (the formation of giant cells) is determined.

Figure 2:
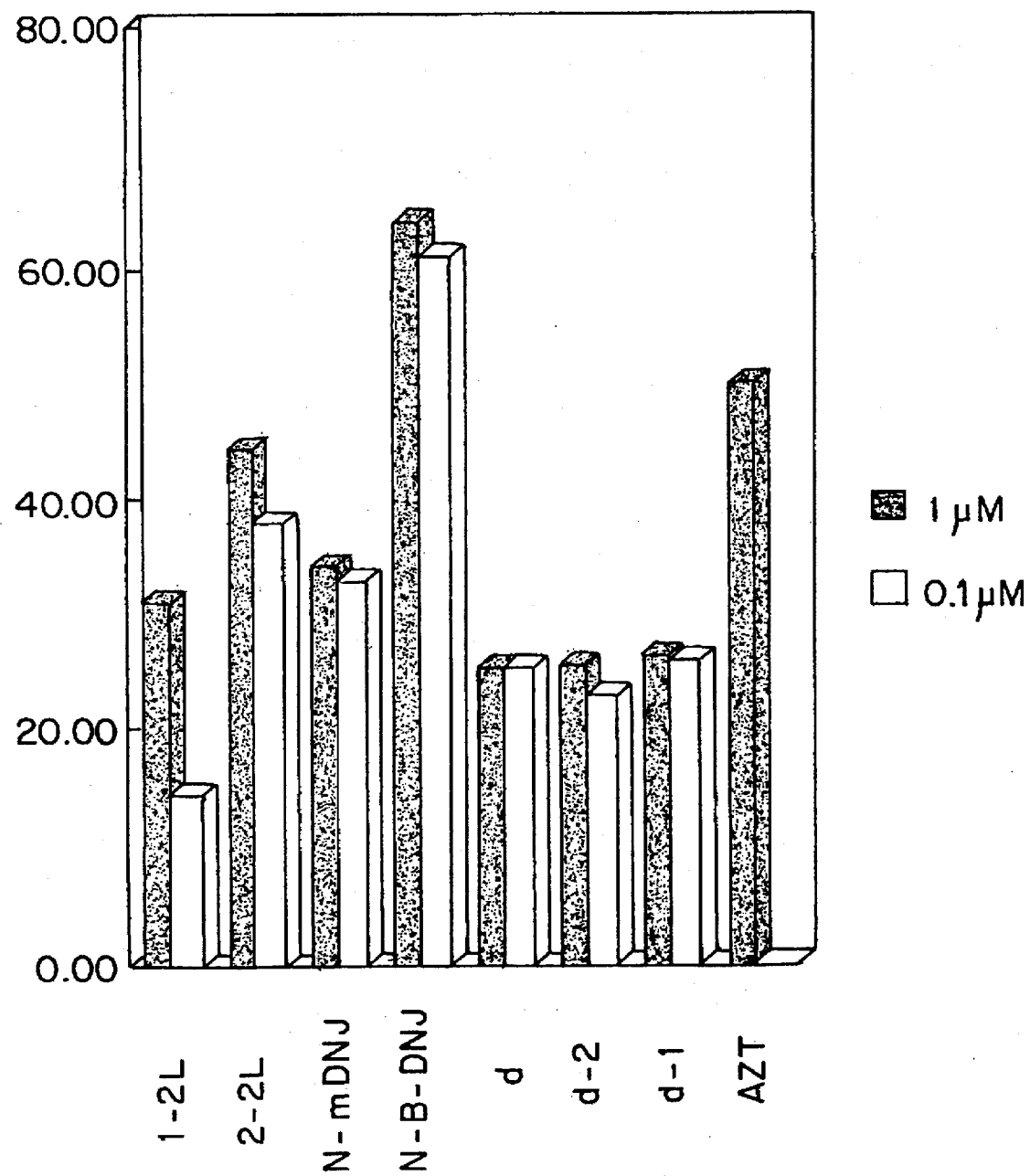
FIG. 2 is a graph showing the inhibitory effects on cell fusion (the formation of giant cells) by the cocultivation of HIV-infected Molt-4/C18 cells with Molt-4/IIIB cells.

FIG. 2 shows the results. The ordinate refers to the inhibition ratio (%). As FIG. 2 shows, the compounds of the present invention have anti-HIV activities.

TEST EXAMPLE 5

As Tables 1 and 2 show, it is proved that the compounds (d), (1-1L), (1-2L), (2-2L), (d-1) and (d-2) of the present invention have remarkably strong inhibitory activities against α-glucosidase, compared with the known deoxynojirimycin having inhibitory activity. In particular, the compounds (1-1L), (1-2L) and (2-2L) have weak inhibitory activities against β-glucosidase, which indicates that these compounds are highly specific α-glucosidase inhibitors. Further, these compounds were examined in cytotoxicity.

A 20 mM aqueous solution of the compound (d), a 10 mM solution of the compound (1-1L) in 50% DMSO and a 10 mM solution of the compound (1-2L) in 50% DMSO were prepared and employed as test samples.

By using a 12-well microplate (3.8 cm²/well, manufactured by Corning), B16 melanoma cells were incubated in Dulbecco-modified Eagle medium (manufactured by Gibco Laboratories) containing 10% fetal calf serum (FCS) at a density of $2 \times 10^5$ cells/ml/well at 37° C. under 5% $CO_2$. After 24 hours, the medium was replaced with Dulbecco-modified Eagle medium containing each sample. The incubation was continued under the same conditions for additional 24 hours. Then the cells were harvested by adding EDTA, washed with PBS and stained with 0.3% Trypan blue solution to thereby determine the survival ratio of the cells.

As Table 3 shows, no cytotoxicity was observed in any concentration range examined. The compound (1-2L) showed no cytotoxicity even at a concentration 10,000 times as high as the 50% inhibitory concentration ($IC_{50}$) of α-glucosidase, which suggests that it is useful as a drug with a high safety.

TABLE 3

| Compound | Compound concentration (μM) | | | |
|---|---|---|---|---|
| | 100 | 50 | 10 | 5 |
| d | — | — | — | — |
| 1-1L | — | — | — | — |
| 1-2L | — | — | — | — |

Survival ratio determined by staining with 0.3% Trypan blue solution (control: 100%).

+: 25%, ±: 50%, −: >95%.

While the invention has been described in detail and with reference to specific embodiments thereof, it will be apparent to one skilled in the art that various changes and modifications can be made therein without departing from the spirit and scope thereof.

What is claimed is:

1. An aminocyclopentane derivative represented by the formula (1):

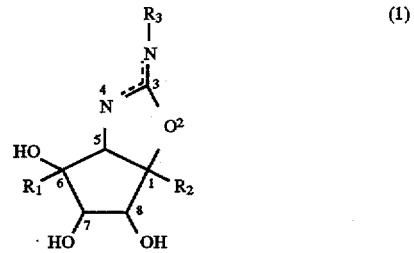

wherein $R_1$ represents H while $R_2$ represents $CH_2OH$, or $R_1$ represents $CH_2OH$ while $R_2$ represents H; and $R_3$ represents a substituted or unsubstituted aryl group or an alkyl, alkenyl, alkynyl or hydroxyalkyl group having 1 to 10 carbon atoms.

2. An aminocyclopentane derivative as claimed in claim 1 wherein, in the aminocyclopentane derivative represented by the above formula (1), $R_3$ represents a substituted or unsubstituted aryl group.

3. An aminocyclopentane derivative as claimed in claim 2, wherein the aminocyclopentane derivative represented by the above formula (1) is selected from the group consisting of (1S,5R,6S,7S,8R)-6-hydroxymethyl-3-phenylamino-2-oxa-4-azabicyclo[3.3.0]oct-3-ene-6,7,8-triol represented by the following structural formula (1-1L), (1R,5S,6R,7R,8S)-6-hydroxymethyl-3-phenylamino-2-oxa-4-azabicyclo[3.3.0]oct-3-ene- 6,7,8-triol represented by the following structural formula (1-D), (1S,5R,6S,7R,8S)-1-hydroxymethyl-3-phenylamino-2-oxa-4-azabicyclo[3.3.0]oct-3-ene-6,7,8-triol represented by the following structural formula (1-2L) and (1R,5S,6R,7S,8R)-1-hydroxymethyl-3-phenylamino-2-oxa-4-azabicyclo[3.3.0]oct-3-ene-6,7,8-triol represented by the following structural formula (1-2D):

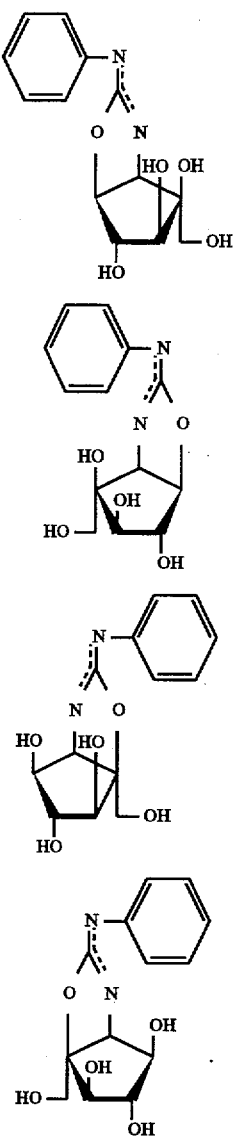
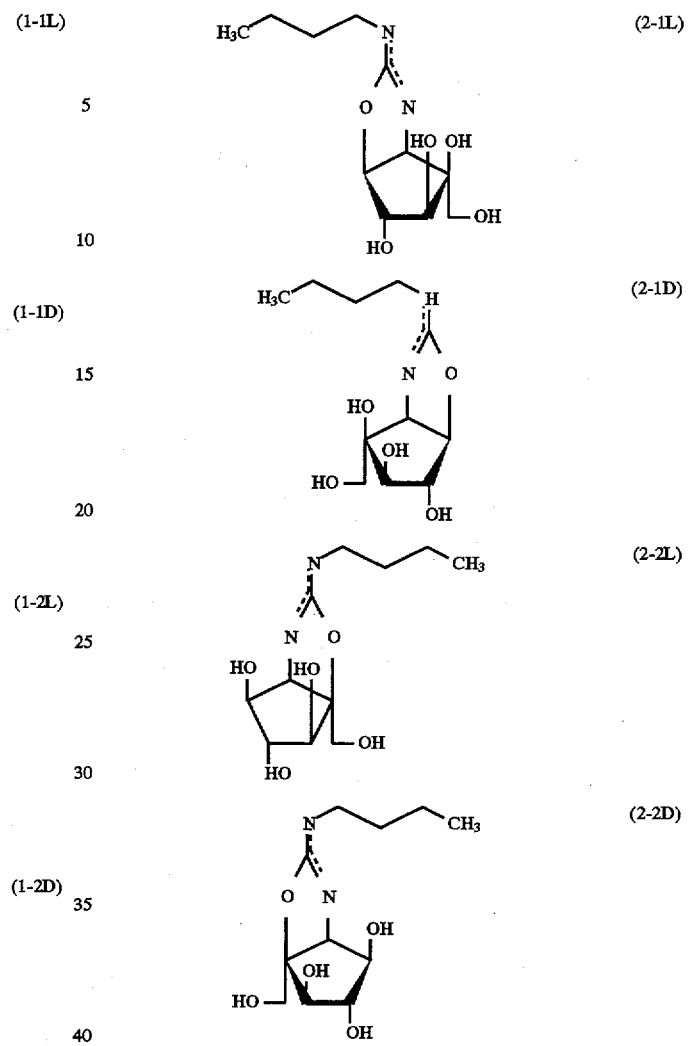

4. An aminocyclopentane derivative as claimed in claim 1, wherein, in the aminocyclopentane derivative represented by the above formula (1), $R_3$ represents an alkyl group having 1 to 10 carbon atoms.

5. An aminocyclopentane derivative as claimed in claim 4, wherein the aminocyclopentane derivative represented by the above formula (1) is selected from the group consisting of (1S,5R,6S,7S,8R)-6-hydroxymethyl-3-butylamino-2-oxa-4-azabicyclo[3.3.0]oct-3-ene-6,7,8-triol represented by the following structural formula (2-1L), (1R,5S,6R,7R,8S)-6-hydroxymethyl-3-butylamino-2-oxa-4-azabicyclo[3.3.0]oct-3-ene-6,7,8-triol represented by the following structural formula (2-1D), (1S,5R,6S,7R,8S)-1-hydroxymethyl-3-butylamino-2-oxa-4-azabicyclo[3.3.0]oct-3-ene-6,7,8-triol represented by the following structural formula (2-2L) and (1R,5S,6R,7S,8R)-1-hydroxymethyl-3-butylamino-2-oxa-4-azabicyclo[3.3.0]oct-3-ene-6,7,8-triol represented by the following structural formula (2-2D):

6. A glycosidase inhibitor composition which comprises an aminocyclopentane derivative represented by formula (1):

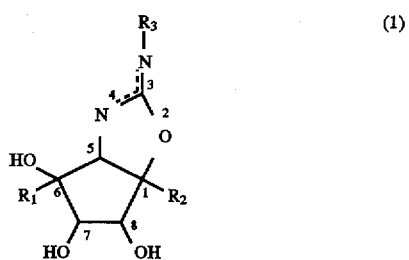

wherein $R_1$ represents H while $R_2$ represents $CH_2OH$, or $R_1$ represents $CH_2OH$ while $R_2$ represents H; and $R_3$ represents a substituted or unsubstituted aryl group or an alkyl, alkenyl, alkynyl or hydroxyalkyl group having 1 to 10 carbon atoms, as an active ingredient, and a pharmaceutically acceptable carrier.

7. The glycosidase inhibitor composition as claimed in claim 6, wherein said glycosidase inhibitor is an α-glucosidase inhibitor.

8. The glycosidase inhibitor composition as claimed in claim 7, wherein said aminocyclopentane derivative is represented by formula (1)

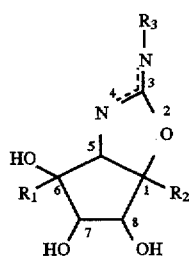

(1)

wherein $R_1$ represents H while $R_2$ represents $CH_2OH$, or $R_1$ represents $CH_2OH$ while $R_2$ represents H; and $R_3$ represents a substituted or unsubstituted aryl group or an alkyl group having 1 to 10 carbon atoms.

9. The glycosidase inhibitor composition as claimed in claim 8, wherein said aminocyclopentane derivative is selected from the group consisting of (1S,5R,6S,7S,8R)-6-hydroxymethyl-3-phenylamino-2-oxa-4-azabicyclo[3.3.0]oct-3-ene-6,7,8-triol represented by the following structural formula (1-1L), (1R,5S,6R,7R,8S)-6-hydroxymethyl-3-phenylamino-2-oxa-4-azabicyclo[3.3.0]oct-3-ene-6,7,8-triol represented by the following structural formula (1-1D), (1S,5R,6S,7R,8S)-1-hydroxymethyl-3-phenylamino-2-oxa-4-azabicyclo[3.3.0]oct-3-ene-6,7,8-triol represented by the following structural formula (1-2L), (1R,5S,6R,7S,8R)-1-hydroxymethyl-3-phenylamino-2-oxa-4-azabicyclo[3.3.0]oct-3-ene-6,7,8-triol represented by the following structural formula (1-2D):

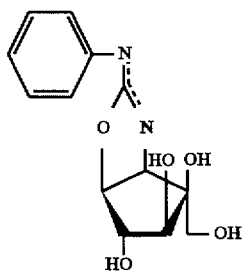

(1-1L)

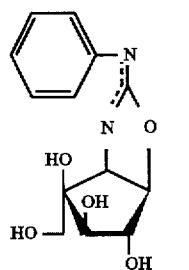

(1-1D)

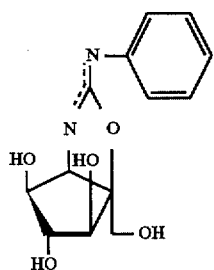

(1-2L)

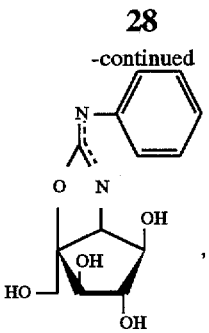

(1-2D)

(1S,5R,6S,7S,8R)-6-hydroxymethyl-3-butylamino-2-oxa-4-azabicyclo[3.3.0]oct-3-ene-6,7,8-triol represented by the following structural formula (2-1L), (1R,5S,6R,7R,8S)-6-hydroxymethyl-3-butylamino-2-oxa-4-azabicyclo[3.3.0]oct-3-ene-6,7,8-triol represented by the following structural formula (2-1D), (1S,5R,6S,7R,8S)-1-hydroxymethyl-3-butylamino-2-oxa-4-azabicyclo[3.3.0]oct-3-ene-6,7,8-triol represented by the following structural formula (2-2L), and (1R,5S,6R,7S,8R)-1-hydroxymethyl-3-butylamino-2-oxa-4-azabicyclo[3.3.0]oct-3-ene-6,7,8-triol represented by the following structural formula (2-2D):

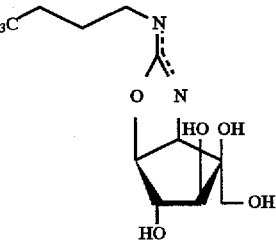

(2-1L)

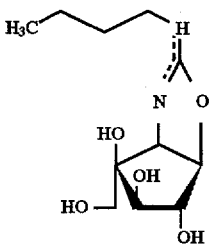

(2-1D)

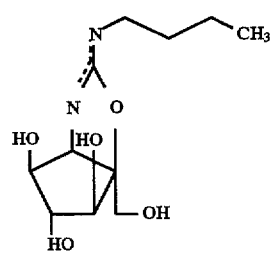

(2-2L)

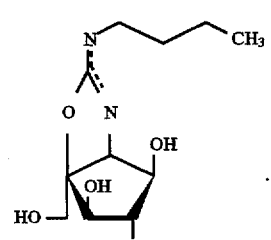

(2-2D)

10. The aminocyclopentane derivative as claimed in claim 1, wherein $R_1$ represents H and $R_2$ represents $CH_2OH$, and the aminocyclopentane derivative represented by formula (1) is a (1S,5R,6S,7R,8S)-compound.

11. The glycosidase inhibitor composition as claimed in claim 6, wherein $R_1$ represents H and $R_2$ represents $CH_2OH$, and the aminocyclopentane derivative represented by formula (1) is a (1S,5R,6S,7R,8S)-compound.

* * * * *